United States Patent [19]

Tanaka et al.

[11] Patent Number: 5,401,647

[45] Date of Patent: Mar. 28, 1995

[54] METHOD OF PREPARING LIMULUS AMOEBOCYTE LYSATE

[75] Inventors: Shigenori Tanaka; Jun Aketagawa; Yuko Shibata, all of Tokyo, Japan

[73] Assignee: Seikagaku Kogyo Kabushiki Kaisha (Seikagaku Corporation), Tokyo, Japan

[21] Appl. No.: 859,411

[22] PCT Filed: Sep. 27, 1991

[86] PCT No.: PCT/JP91/01308

§ 371 Date: May 27, 1992

§ 102(e) Date: May 27, 1992

[87] PCT Pub. No.: WO92/06381

PCT Pub. Date: Apr. 16, 1992

[30] Foreign Application Priority Data

Sep. 27, 1990 [JP] Japan .................. 2-255201

[51] Int. Cl.$^6$ .................. C12N 11/06; C12N 11/08; C12N 11/14; C12Q 1/37

[52] U.S. Cl. .................. 435/176; 435/23; 435/179; 435/180; 435/181; 436/175; 536/117; 536/118; 536/119

[58] Field of Search .................. 435/4, 18, 23, 176, 435/177, 178, 179, 180, 181, 184, 100, 101, 104; 436/175; 536/119, 120, 121, 117, 118

[56] References Cited

U.S. PATENT DOCUMENTS 4,270,152 11/1990 Ashida et al. .................. 435/23 X
4,454,315 6/1984 Sasaki et al. .................. 536/120 X
5,155,032 10/1992 Tanaka et al. .................. 435/184

FOREIGN PATENT DOCUMENTS 0333187 9/1989 European Pat. Off. .
59-28474 2/1984 Japan .

OTHER PUBLICATIONS

Tanaka et al., "Activation of a Limulus Coagulation Factor G by (1-3)-β-D-flucans.", *Carbohydrate Research.*, 218(1991)., pp. 167-174.
Tanaka et al., "Inhibition of High Molecular Weight (1-3)-β-D-glucan Dependant Activation of a Limulus Coagulation Factor G by Laminaran Oligosaccharides & Curdlan Degradation Products"., *Carbohydrate Research.*, 244 (1993)., pp. 115-127.
Biological Abstracts, vol. 91, No. 10, May 15, 1991, Abstract No. 108553.
N. Ohno et al., "Reactivity of Limulus Amoebocyte Lysate Towards (1-3)-β-D-glucans," *Carbohydrate Research*, vol. 207, No. 2, Oct. 25, 1990, pp. 311-318.

*Primary Examiner*—Robert J. Warden
*Assistant Examiner*—L. M. Crawford
*Attorney, Agent, or Firm*—Sughrue, Mion, Zinn, Macpeak & Seas

[57] ABSTRACT

Disclosed is a method of preparing limulus amoebocyte lysate substantially free from factor G which comprises bringing limulus amoebocyte lysate into contact with an insoluble carrier on which a (1→3)-β-D-glucoside structural portion represented by the following formula [I] produced by depolymerizing and/or fractionating a carbohydrate chain is immobilized:

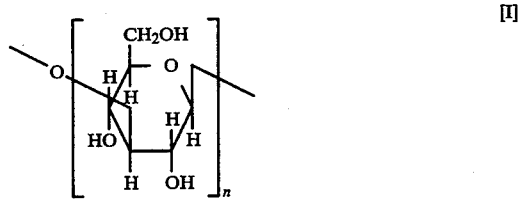

wherein n represents an integer of 2 to 370.

5 Claims, 3 Drawing Sheets

METHOD OF PREPARING LIMULUS AMOEBOCYTE LYSATE

SUMMARY OF THE INVENTION

The present invention relates to a method of preparing limulus amoebocyte lysate.

BACKGROUND OF THE INVENTION

It has been widely known that limulus amoebocyte lysate (hereinafter referred to as LAL) reacts with an endotoxin which is a bacterial pyrogen (hereinafter referred to as endotoxin) to cause a coagulation.

On the basis of this reaction, various methods of assaying endotoxin have been developed.

Figure 1:
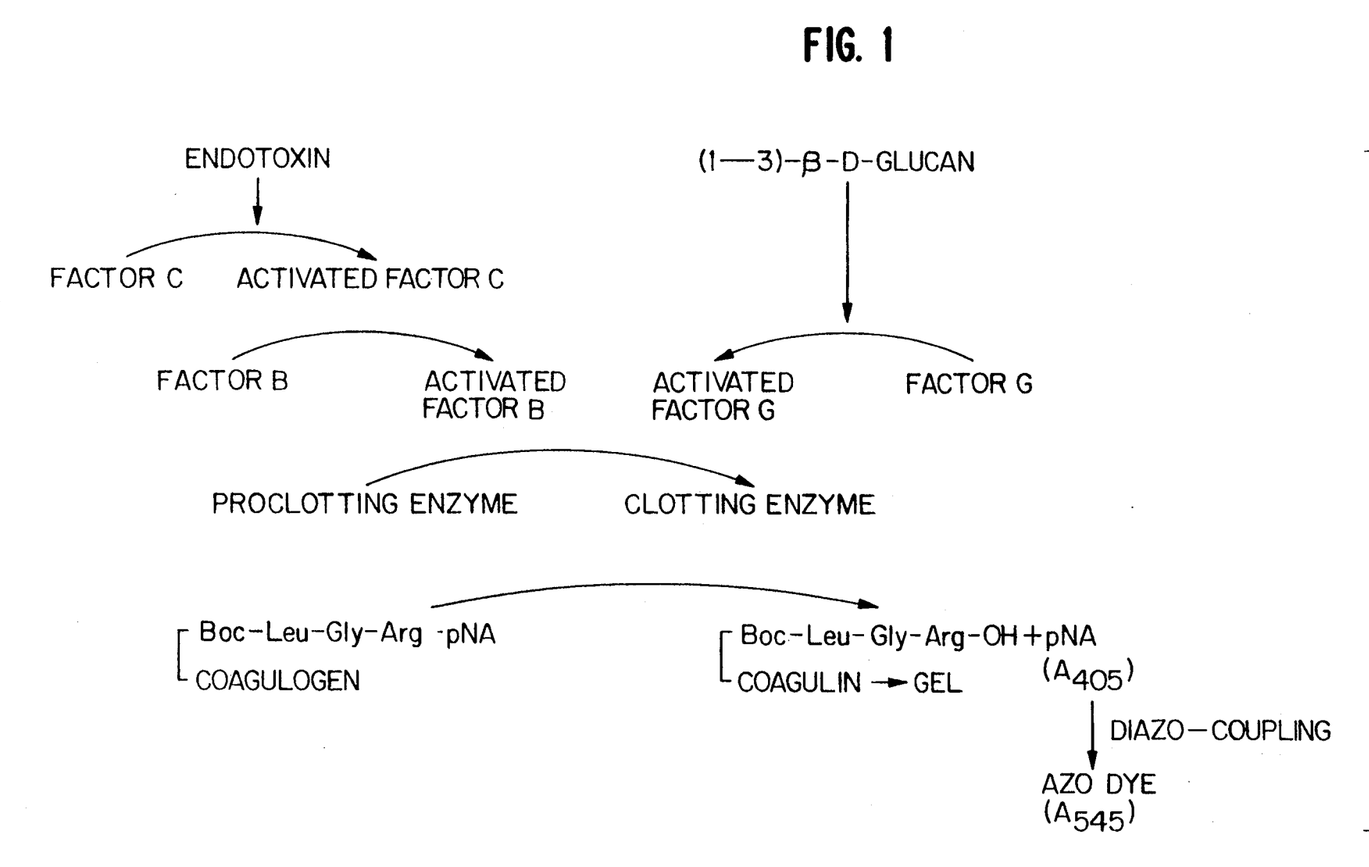
FIG. 1 shows a reaction mechanism of a limulus amoebocyte lysate coagulation system.

Recently, the above-described coagulation reaction mechanism has been elucidated, i.e., coagulogen is converted to coagulin to cause a coagulation (gelation) according to a stepwise reaction as shown in FIG. 1 [S. Iwanaga et al., The hemolymph coagulation system in invertebrate animals, J. Protein Chem., 5, 255-268 (1986)]. It can be understood that the reaction mechanism includes two coagulation systems: a system initiated by endotoxin (factor C system) and a system initiated by (1→3)-β-D-glucan (e.g., curdlan, partially carboxyfnethylated (1→3)-β-D-glucan) (factor G system).

The present inventors already found that the (1→3)-β-D-glucan structural portion having a particular molecular weight inhibits the activation of the system of LAL initiated by (1→3)-β-D-glucan (factor G system), and filed the patent application as a limulus amoebocyte lysate factor G activation inhibitor (Japanese Patent Application No. 63-216341 and WO 90/02951).

However, when this inhibitor is added to LAL in order to obtain LAL specific to endotoxin, a complex comprising the inhibitor and factor G remaining in LAL is possibly dissociated with a sample added and the liberated factor G is activated by a factor G-activating substance.

DETAILED DESCRIPTION OF THE INVENTION

An object of the present invention is to provide LAL free from factor G which is first activated with (1→3)-β-D-glucan in the LAL coagulation mechanism.

Thus, the present invention provides a method of preparing limulus amoebocyte lysate substantially free from factor G which comprises contacting limulus amoebocyte lysate with an insoluble carrier on which (1→3)-β-D-glucoside structural portion having formula [I] is fixed.

[I]

wherein n represents an integer of 2 to 370.

The (1→3) -β-D-glucoside structural portion used in the present invention is a polyglycoside having, in one molecule, at least one poly-(1→3)-β-D-glucoside structural portion [hereinafter referred to as a poly(1→3)-glucoside moiety] comprising 2 to 370, preferably 3 to 310, and more preferably 4 to 180 consecutive (1→3)-β-D-glucoside structural units (molecular weight: 162) represented by the following formula.

(I)

Thus, the polyglycoside used in the present invention is required to have at least one poly(1→3)glucoside moiety in one molecule. For example, the polyglycoside used in the present invention may consists substantially of one poly(1→3)glucoside moiety, for example, poly-(1→3)-β-D-glucoside represented by the following formula

(I-1)

wherein n is an integer of 2 to 370, preferably 3 to 310, and more preferably 4 to 180. Alternatively, it may be of a structure in which one poly(1→3)glucoside moiety has a carbohydrate chain, which may be bound to the above-described poly(1→3)glucoside moiety as a branched chain, composed of one or more (1→4)-β-D-glucoside structural units represented by the following formula;

(II)

one or more (1→6 )-β-D-glucoside structural unit represented by the following formula;

(III)

or one or more modified β-D-glucoside structural unit represented by the following formulae;

(IV)

(V)

(VI)

wherein at least one of $R_1$, $R_2$ and $R_3$ represent(s) a chemically introducible group(s), i.e., a methyl group, a hydroxyalkyl group such as a hydroxymethyl group, a carboxyalkyl group such as a carboxymethyl group, an acetyl group, a sulfate group, a phosphate group, or an allyl group, a metal salt of any of the above-mentioned groups, an ammonium salt and an organic amine salt of any of the above-mentioned groups, and the remaining groups represent a hydrogen atom.

Further, the polyglycoside used in the present invention may have a structure in which two or more of the above-described poly(1→3)glucoside moieties are linked to each other via the other carbohydrate moieties as shown by the following formula wherein each of $A_1$, $A_2$, ... represents a poly(1→3)-$\beta$-D-glucoside moiety having 2 to 370, preferably 3 to 310 and, more preferably 4 to 180 (1→3)-$\beta$-D-glucoside structural units represented by the above formula (I) continuously bound to one another, the number of the units of formula (I) constituting each moiety of $A_1$, $A_2$, ... may be different from each other, and $B_1$, $B_2$, ... each represent the same or different carbohydrate chain moieties as set forth above. The other carbohydrate chain structural portions represented by $B_1$, $B_2$, ... may be, for example, a structural moiety composed of one structural unit represented by the above-described formula (II), (III), (IV), (V) or (VI) or two or more such structural units.

Furthermore, the polyglycoside used in the present invention may have such a structure that the above-described poly(1→3)glucoside moiety is linked to a long-chain poly(1→3)-$\beta$-D-glucoside structural portion composed of 371 or more consecutive (1→3)-$\beta$-D-glucoside structural units represented by the above-described formula (I), via the other carbohydrate chain structures as shown by the above-described $B_1$, $B_2$, ...

Accordingly, the polyglycoside used in the present invention contains at least one of the above-described poly(1→3)glucoside moieties per molecule, and its molecular weight is not particularly limited.

Further, it is preferred that the polyglycoside used in the present invention substantially comprises at least one above-described poly(1→3)glucoside moiety per molecule, but it should not be limited thereto. For example, it may also contain other polyglycosides including a high molecular weight poly(1→3)-$\beta$-D-glucoside moiety having consecutive 371 or more (1→3)-$\beta$-D-glucoside structural units represented by the above-described formula (I). This is because the polyglycoside according to the present invention is more rapidly and more strongly bound to factor G which is an initiation factor of a factor G activation system of LAL, than a high molecular weight poly(1→3)-$\beta$-D-glucoside which is a factor G activating substance used to thereby inhibit the activation of factor G to an activated factor G. Therefore, the presence of such high molecular weight poly(1→3)-$\beta$-D-glucoside does not substantially affect the inhibition action of the polyglycoside of the present invention.

The molecular weight of the polyglycoside used herein is determined by performing gel permeation chromatography using a standard substance of known molecular weight under the following conditions to prepare a calibration curve, subjecting a test sample to gel permeation chromatography under the same conditions, and comparing the results with the calibration curve.

Column: TSKgel G-PWXL series (Tosoh Corporation), 7.8×300 mm several columns of several types, Mobile phase: 0.3M NaOH Flow rate: 0.5 ml/min Sample solution concentration: 0.1 to 5 mg/ml Sample solution volume injected: 0.1 ml Column temperature: room temperature Detection method: measurement by a differential refractometer (LKB Co.) or quantitative analysis of carbohydrate by the phenol-sulfuric acid method Standard substance: TSK standard polyethylene oxide (Tosoh Corporation) and polyethylene glycol (Nacalai Tesque), 10 types having an average molecular weight ranges 1,000 to 860,000

The polyglycosides of the present invention as defined above may be derived from natural sources or may be synthesized. They also may be partially chemically modified products of poly(1→3)-$\beta$-D-glucoside having three or more (1→3)-$\beta$-D-glucoside structural units represented by the above-described formula (I). Usually, those derived from natural sources are readily available. Examples of such polyglycoside are described below.

(1) substantially straight-chain polyglucosides consisting substantially of the (1→3)-$\beta$-D-glucoside structural units represented by the above formula (I) such as (1→3)-$\beta$-D-glucans derived from bacteria of the genus Alcaligenes, paramylon derived from flagellates Euglena, $\beta$-glucans from fibrous tissues of higher plants or callose extracted from sieve tubes of higher plants, D-glucose polymers having (1→3)-$\beta$-bonds and contained in partially hydrolyzed products of laminatans derived from brown algae of the genus Laminaria and Eisenia or the above-described (1→3)-$\beta$-D-glucan, laminaridextrins having a polymerization degree of 10 to 20, laminarioligosaccharides having a polymerization degree of 10 or less, etc.

(2) Polyglycosides comprising the (1→3)-β-D-glucoside structural units represented by the above formula (I) and the (1→6)-β-D-glucoside structural units represented by the above formula (III) exemplified by:
   a) polyglycosides having a main carbohydrate chain of (1→3)-β-bonds incorporating one to several glucoses connected by the (1→6)-β-bond, for example, laminatans derived from brown algae of the genus Eisenia;
   b) polyglycosides as described in above a), in which a carbohydrate chain of the (1→3)-β-bonds is linked to the glucose or the glucose polymers as a branched chain through the (1→6)-β-bond, which may further partially include other carbohydrate portions, for example, laminarans derived from brown algae of the genus Laminaria, chrysolaminarans derived from diatoms such as Ochromonas, Phaeodactylum, Skeletonema, Biddulphia, Coscinodiscus, and Chaetoceros and pachyman derived from Poria;
   c) polyglycosides having many more branches and being dendriform such as β-glucan contained in the cell walls of Ascomycetes, Basidiomycetes and Phycomycetes, for example, glucans derived from the cell wall of Phytophthora, etc.;
   d) polyglycosides having a straight chain (1→3)-β-glucan to which glucose is linked through the (1→6)-β-bond, for example, sclerotan derived from Sclerotinia having a glucosyl branch on every three glucosyl residues of the main chain, schizophytlan derived from Schizophyllum, grifolan LE derived from *Grifola frondosa,* scleroglucans derived from Sclerotium, Corticium and Stromatinia, etc. or those having a straight chain (1→3)-β-glucan to which glucoses are linked through the (1→6)-β-bond at a rate of two glucosyl residues per five glucosyl residues of the main chain, for example, lentinan derived from Lentinus, etc., and
   e) polyglycosides having a straight chain (1→6)-β-glucan having plural glucose branches from the C-3 position of glucose residues of the main chain through the (1→3)-β-bond, for example, β-glucan derived from the cell wall of Saccharomyces (bakers' yeast), etc.

(3) Polyglycosides having both the (1→3)-β-D-glucoside structural units represented by the above formula (I) and the (1→4)-β-D-glucoside structural units represented by the above formula (II), for example, lichenans derived from Cetraria, Usnea, Evernia, etc., β-glucans contained in barley endosperm, etc., which are composed of a carbohydrate chain comprising oligoglucosides linked to each other through the (1→3)-β-bond and having (1→3)-β-oligoglucosides at intervals.

Some of the above-described polyglycosides are commercially available and can be used as is. If necessary, the polyglycosides are used following a partial decomposition and/or a fractionation treatment to prepare a fraction rich in a polyglycoside containing the (1→3)-β-D-glucoside structural unit represented by the above formula (I) in the above specified amount.

Such partial decomposition and fractionation treatment can be effected according to a known method. For example, partial decomposition of carbohydrate chains can be effected by hydrolysis with an acid, an alkali or β-glucanase, acetolysis, sonication or the like. A molecular weight fractionation can be effected by precipitation with an organic solvent such as alcohol, acetone and ether, or salts, or a fractionation using a molecular sieve agent or a molecular sieve membrane.

Further, a part of the carbohydrate chains of the polyglycoside as exemplified in the above (1) to (3) may be chemically modified with an alkyl group such as a methyl group, a hydroxyalkyl group such as a hydroxymethyl group, a carboxyalkyl group such as a carboxymethyl group, an acidic group such as an acetyl group, a sulfate group or a phosphate group, or other functional groups. They can be prepared by introducing these functional groups according to a known method [for example, (1) Seikagakukenkyuho (Methods of Studying Biochemistry) I, edited by Ando, Terayama, Nishizawa and Yamakawa, 284–303 (1967), Asakura Shoten, (2) Whistler, R. L. ed.: Methods in Carbohydrate Chemistry III, 193–267, 271–331 (1964), Academic Press, etc.]. Particularly, (1→3)-β-D-glucan having a molecular weight of about 60,000 or more and having factor G activating action becomes usable if it is subjected to a partial chemical modification so as to adjust the number of the (1→3)-β-D-glucoside structural units represented by the above formula (I) in the poly(1→3)-β-D-glucoside moiety to 370 or less.

Thus, suitable examples of the polyglycosides of the present invention are as follows:

Laminarioligosaccharide having a molecular weight of 342 to 1,638;
Laminaridextrin having a molecular weight of 1,800 to 3,258;
(1→3)-β-D-glucan having an average molecular weight of 2,000 to 60,000;
Laminaran having an average molecular weight of 3,000 to 23,000;
Sclerotan having an average molecular weight of 3,000 to 20,000;
Schizophyllan having an average molecular weight of 500,000 or less;
Lentinan having an average molecular weight of 1,100,000 or less;
Bakers' yeast-derived water-soluble glucan having an average molecular weight of 12,000 or less;
Lichenan having an average molecular weight of 33,000 or less;
Barley β-glucan having an average molecular weight of 200,000 or less;
Partially carboxymethylated (1→3)-β-D-glucan (substitution degree: 0,003 to 1.0) having an average molecular weight of 40,000 to 240,000 obtained by, for example, a partial carboxymethylation of curdian and salts thereof;
Partially carboxymethylated laminaran (substitution degree: 1.0 or less) having an average molecular weight of 23,000 or less and salts thereof;
Partially methylated (1→3)-β-D-glucan (substitution degree: 0.003 to 1.0) having an average molecular weight of 80,000 or less;
Partially sulfated laminaran (substitution degree: 1.0 or less) having an average molecular weight of 23,000 or less and salts thereof.

Any insoluble carrier can be used for immobilization of the above-described (1→3)-β-D-glucoside structural portion having the poly(1→3)glucoside moiety as long as it has hydrophilic groups such as a hydroxy group and a carbamoyl group. Examples of these insoluble carriers are as follows: cellulose such as cellulose powder (available from Advantec Toyo), Cellulofine (available from Seikagaku Corporation), Avicel (available from Funakoshi Pharmaceutical), Cellex (available from Bio-Rad); agarose such as Sepharose (available from Pharmacia), Biogel A (available from Bio-Rad ), Chromagel A (available from Dojindo Laboratories), Sagavac (available from Seravac Laboratories), Gelarose (available from Litex), P-L Agarose (available from P-L Biochemicals); cross-linked dextran such as Sephadex G and Sephacryl (available from Pharmacia), P-L Dex (available from P-L Biochemicals); polyacrylamide such as Biogel P (available from BioRad), Chromagel P (available from Dojindo Laboratories); porous glass such as Bioglass (available from Bio-Rad); hydrophilic polyvinyl synthetic polymer such as Toyopearl (available from Tosoh).

For immobilizing the (1→3)-β-D-glucoside structural portion on these insoluble carriers, these carriers are required to be activated. There may be mentioned various activation methods including, for a carrier having hydroxyl groups, a cyanogen bromide method (R. Axen, J. Porath, and S. Ernback, Nature, 214, 1302 (1967)) and a method using oxiranes (J. Porath and N. Fornstedt, J. Chromatogr., 51, 479 (1970) and L. Sundberg and J. Porath, J. Chromatogr., 90, 87 (1974)), for a carrier having carbamoyl groups, a method using an alkyl diamine to convert the carrier to an aminoalkylamine derivative, and a method using hydrazine to convert the carrier to a hydrazine derivative (both described in J. K. Inman and H. M. Dintzis, Biochemistry, 8, 4074 (1969)). In view of stability and decreased non-specific absorption, excellent is a method which comprises epoxy-activating a carrier with epichlorohydrin or bisoxiranes, reacting the resulting epoxy-activated insoluble carrier with hydrazine hydrate or dihydrazide compound to obtain a hydrazine derivative or a dihydrazide derivative, which serves as an activated product (Isamu Matsumoto et al. JP-A-59-15401).

LAL used in the method according to the present invention is not particularly limited as long as it is extracted from limulus blood corpuscles and the factor C system thereof is activated in a reaction with endotoxin. Usable as such LAL include commercially available products such as a freeze-dried product of LAL, a freeze-dried product of LAL with a synthetic substrate and the like.

Various commercially available lysate are as follows: Pregel, Pregel-S, Pregel-M, Pyrodick, Toxicolor (all available from Seikagaku Corporation), Limulus II-Test Wako, Limulus II-single Test Wako, Limulus HS II-Test Wako, Limulus HS II-single Test Wako, Limulus S II-single Test Wako, Limulus amoebocyte lysate II (freeze-dried product), Limulus amoebocyte lysate-HS II (freeze-dried product) (all available from Wako Pure Chemical Industries), Pyrotell (available from Cape Cod), Pyrosate (available from Haemachem), Pyrogent®, pyrogent® Plus, Pyrogent® Single Test, Pyrogent® Multitest, LAL Single Test Kit, QCL-1000, Kinetic QCL ™ (all available from Whittaker Bioproducts), Coatest® Endotoxin (Kabi Bitrum).

The method of preparing the (1→3)-β-D-glucoside structural portion used in the present invention is further illustrated in more detail below.

The (1→3)-β-D-glucoside structural portion used in the present invention can be prepared, for example, by the method described in the following preparation examples. Commercially available (1→3)-β-D-glucan products fallen within the scope of the present invention can be used as it is.

PREPARATION EXAMPLE 1

Preparation from commercially available curdlan by means of molecular sieve chromatographic-fractionation

Figure 2:
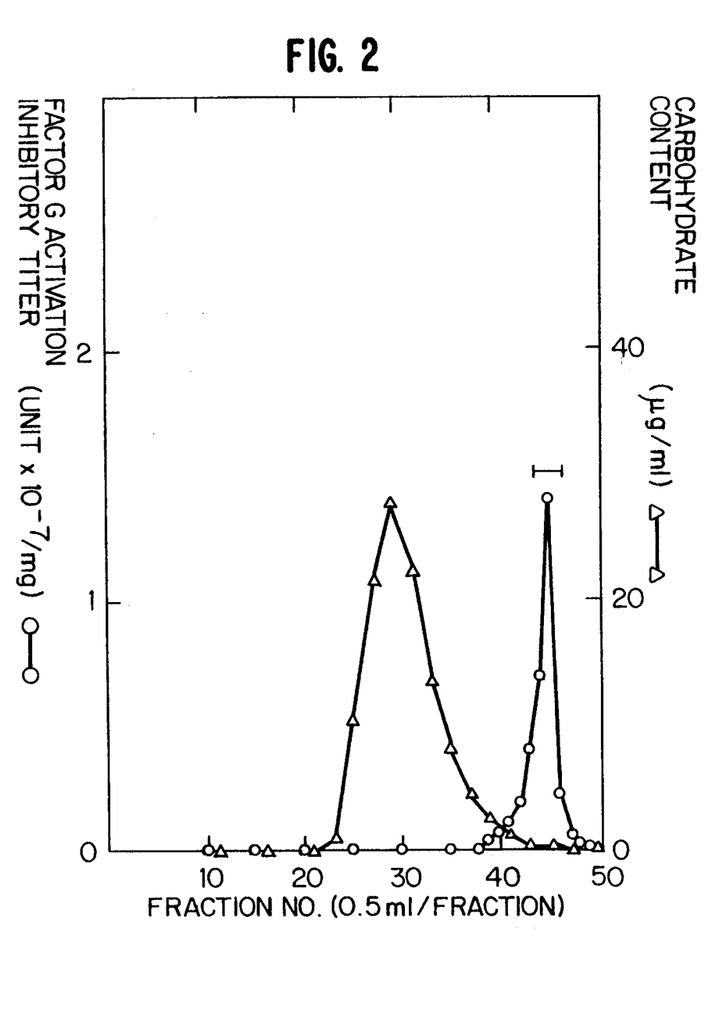
FIG. 2 shows a fraction pattern (elution curve) of a commercially available curdlan obtained by a molecular sieve chromatography. The symbol ◯ stands for factor G activation inhibition titer (left side, ordinate axis) and Δ stands for a sugar content.
Figure 3:
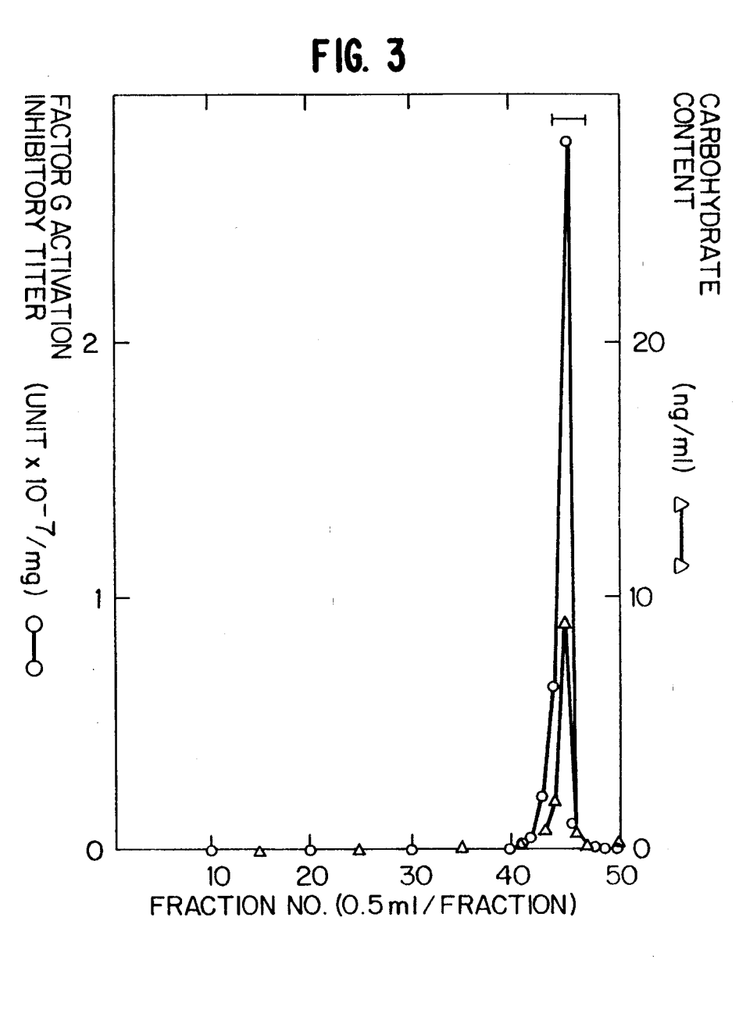
FIG. 3 shows a fraction pattern of rechromatographed fraction Nos. 44 to 46 of FIG. 2. The symbol ◯ stands for factor G activation inhibition titer (left side, ordinate axis) and Δ stands for a carbohydrate content.

One gram of curdlan (Wako Pure Chemical Industries, Lot No. PEQ 9080, Mn>136,000, Mw/Mn>2.76, sample. No. 101) was dissolved in 0.3M NaOH (5 mg/ml). Each 100 microliter aliquot of the resulting solution was subjected to gel permeation chromatography (hereinafter abbreviated as GPC) at room temperature under the following conditions. {Columns: TSKgel G6000PW$_{XL}$ and G5000PW$_{XL}$ (both 7.8×300 mm) are connected in series, mobile phase: 0.3M NaOH, flow rate: 0.5 ml/min}. The eluted low molecular fraction (Nos. 44 to 46) was collected, which was then further subjected to a chromatography to obtain 0.015 mg of a sample (sample No. 1) having the number average molecular weight of 3,050 and the polydispersity of 1.29. The above-described GPC fraction pattern is shown in FIG. 2. Fraction patterns obtained by a rechromatography of fraction Nos. 44 to 46 in FIG. 2 are shown in FIG. 3.

The present sample No. 1 was digested with β-1,3-glucanase (Zymolyase-100T, available from Seikagaku Corporation), then, the resulting digest was analyzed by means of GPC (columns: TSKgel G4000PW$_{XL}$, G3000PW$_{XL}$ and G2500PW$_{XL}$ connected in series; mobile phase: distilled water, flow rate: 0.6 ml/min), whereby it could be confirmed that a sugar composition in the digest was glucose 40%, laminaribiose 30%, laminaritriose 20%, laminaritetraose 8%, laminaripentaose 2%, recovery 94%. Thus, it can be seen that the sugar structure of the present sample (No. 1) is β-polyglucoside comprising the (1→3)-β-D-glucoside structural portion.

PREPARATION EXAMPLE 2

Fractionation of curdlan depending on water-solubility

Fifty grams of a commercially available curdlan (sample No. 101) was suspended in a distilled water, and fractionated according to the procedure shown in the following flow sheet.

PREPARATION EXAMPLE 3

Preparation of water-insoluble carbohydrate fraction of curdlan by formic acid decomposition 45 g of the sample No. 102 was subjected to formic acid decomposition according to a method of K. Ogawa et al. [Carbohydr. Res., 29., 397–403 (1973)]. The procedure is shown in the following flow sheet.

PREPARATION EXAMPLE 4-1

Refractionation of water-soluble fraction of formic acid decomposition product of curdlan by molecular sieves 0.15 g of the water-soluble fraction obtained in the above-described Preparation Example 3 (sample No. 3) was dissolved in 30 ml of distilled water, and subjected to GPC (columns: TSKgel G3000PW$_{XL}$×2, G2500PW$_{XL}$×1, mobile phase: distilled water, flow rate: 0.5 ml/min) to collect 0.5 ml fractions. Subsequent rechromatography gave six samples (Nos. 11 to 16) each having a different molecular weight.

PREPARATION EXAMPLE 4-2

Refractionation of water-insoluble fraction of formic acid decomposition product of curdlan by molecular sieves 0.2 g of the water-insoluble fraction obtained in Preparation Example 3 (sample No. 4) was dissolved in 40 ml of 0.3M NaOH solution, and fractionated in the same manner as in the above-described Preparation Example 4-1 using GPC (columns: TSKgel G3000PW$_{XL}$×2, G25000PW$_{XL}$×1, mobile phase: 0.3M NaOH solution, flow rate: 0.5 ml/min), followed by rechromatography. The resulting eluate was neutralized by adding 0.3M HCl solution to obtain two samples each having a different molecular weight (Nos. 17 and 18).

PREPARATION EXAMPLE 5

Preparation of sample from water-insoluble fraction of curdlan by sonication

One gram of the sample No. 102 was suspended in about 100 ml of 5 mM NaOH solution and the suspension was subjected to sonication for 12 minutes at 20 KHz and 80 W under ice-cooling using Sonicator ™ (Model 5202PZT, Ohtake Works, Tokyo) to lower the molecular weight of the sample.

A 5M NaOH solution was added to the resulting suspension so as to give a final concentration of 0.3M NaOH solution. Then, fractionation by chromatography was carried out in the same manner as in the above-described Preparation Example 4-2 to obtain eight samples each having a different molecular weight (Nos. 19 to 22 and 103 to 106).

PREPARATION EXAMPLE 6-1

Preparation of inhibitor derived from seaweed (I)

A sample derived from Eisenia bicyclis was prepared as follows in accordance with the method by T. Usui et al., (Agric. Biol. Chem. 43, 603–611, (1979)). 100 g of a commercially available *Eisensia bicyclis* dried frond (Suita Syoten, Tokyo) was pulverized and subjected to extraction with 80% ethanol to remove a low molecular weight water-soluble fraction. Then, from the resulting residue, a laminaran fraction was extracted using 2% aqueous CaCl$_2$ solution. 95% ethanol was added to the extract to give a final concentration of 75%, and the formed precipitate was collected by centrifugation. After washing with ethanol, a crude laminaran sample was obtained. It was then dissolved in distilled water and treated with an anion exchanger (DEAE-Toyopearl) to remove contaminating acidic substances (alginic acid, etc.) and pigments. Reprecipitation was effected with ethanol to obtain sample No. 25.

PREPARATION EXAMPLE 6-2

Preparation of inhibitor derived from seaweed (II)

A sample derived from *Laminaria japonica* was prepared as follows in accordance with the method described in J. J. Cormell et al., J. Chem. Soc., 3494 (1950). Thus, 100 g of a commercially available Laminaria japonica dried frond (Suita Syoten, Tokyo) was pulverized, a 0.09M HCl solution was added thereto and it was allowed to stand for about three days to effect extraction. Insoluble matters were removed by a filtration and the resulting filtrate was allowed to stand for further one day. A small amount of the precipitate formed was removed by centrifugation. To the supernatant obtained was added 3-fold volume of ethanol so as to give a final concentration of 75%. The precipitate thus formed was collected by centrifugation, washed with alcohol and dried to obtain a water-soluble laminaran fraction (sample No. 27).

PREPARATION EXAMPLE 7-1

Preparation of inhibitor derived from Eumycetes (I)

A sclerotan sample derived from Eumycetes *Sclerotinia libertiana* was prepared as follows in accordance with the method described in Kitahara et al., Res. Bull. Fac. Agric. Gifu University 8, 100–105 (1957). Thus, the defatted dry powder of sclerotium of *Sclerotinia libertiana* (30 g) was subjected to extraction with water. The resulting residue was further subjected to extraction with a 7% NaOH solution and a 10% $CuSO_4$ solution was added to the extract to form precipitate. The resulting precipitate was collected by filtration, washed with hydrochloric acid-acidic methanol to remove copper and then washed with 80% methanol to remove HCl. The residue was purified by three repetitions of washing with methanol and ether and drying to obtain 6 g of sample No. 28.

PREPARATION EXAMPLE 7-2

Preparation of inhibitor derived from Eumycetes (II)

A sample derived from Eumycetes *Schizophyllum commune* was prepared from commercially available schizophyllan (Kaken Chemical, trade name: Sonifilan, medicine Lot No. J61040) in accordance with the method described in K. Tabata et al., Carbohydr. Res., 89, 121–135, (1981). Thus, an aqueous solution of schizophyllan was sonicated for 10 hours in the same manner as in the procedure of the above Preparation Example 5, followed by molecular sieve fractionation under an alkaline condition to obtain three samples different in molecular weight (Nos. 29, 30 and 31).

PREPARATION EXAMPLE 7-3

Preparation of inhibitor derived from Eumycetes (III)

A $\beta$-glucan sample derived from yeast *Saccharomyces cerevisiae* (bakers' yeast) was prepared as follows. Thus, 50 ml of distilled water was added to 90 mg of a commercially available bakers' yeast glucan (Sigma, Lot No. 56F-4027) followed by stirring at room temperature for 2 hours. After centrifugation, about 50 ml of the supernatant was concentrated under a reduced pressure to 1 ml. Insoluble matters were removed by centrifugation. Thus, 0.64 g of sample No. 33 was obtained from the supernatant.

PREPARATION EXAMPLE 8

Preparation of sample derived from barley $\beta$-glucan

A commercially available barley $\beta$-glucan (Sigma, Lot No. 56F-0652) was dissolved in a 0.3M NaOH solution to give a concentration of 5 mg/ml. Then, in accordance with the method described in Preparation Example 4-2, the solution was subjected to molecular sieve fractionation under an alkaline condition to obtain the $\beta$-glucan sample (No. 36) having a narrow molecular weight distribution.

Further, the above-described commercially available $\beta$-glucan was dissolved in a hot water to give a concentration of 5 mg/ml, followed by centrifugation (3,500 rpm, 10 minutes). The supernatant thus obtained was subjected to GPC fractionation (100 $\mu$l per each run, 50 runs) using distilled water as a mobile phase in accordance with the method described in Preparation Example 4-1. The fractionation was repeated under the same conditions to obtain two samples different in molecular weight (sample Nos. 37 and 38).

PREPARATION EXAMPLE 9

Preparation of partially carboxymethylated (1→3)-$\beta$-D-glucan (degree of substitution DS =0.63)

A curdlan water-insoluble product obtained according to Preparation Example 2 was carboxymethylated in accordance with the method described in A. E. Clarke and B. A. Stone: Phytochemistry 1, 175–188 (1962). Thus, 100 g of a curdlan water-insoluble product was dissolved in 1 l of a 5M NaOH solution at 0° C. in nitrogen gas stream. To the resulting solution was added dropwise 236 g of monochloroacetic acid dissolved in 200 ml of water with stirring. After the completion of the addition, stirring was continued for 2 hours at 60° to 65° C. The formed gel was pulverized by vigorous stirring in a 2.5-fold volume of ethanol followed by filtration. The resulting residue was thoroughly washed successively with 70% ethanol, ethanol and ether, and dried. The dried product was dissolved in 7 l of water and neutralized with 1M acetic acid. Then, 40 g of an activated carbon was added thereto and the resulting solution was stirred at room temperature for 1 hour followed by filtration. The filtrate was concentrated under a reduced pressure to 1 l, and 3-fold volume of ethanol was added thereto to form precipitate. The precipitate was washed with ethanol and ether and dried over concentrated sulfuric acid under reduced pressure to obtain 113.85 g of a desired product.

The partially carboxymethylated (1→3)-$\beta$-D-glucan thus obtained was measured for the etherification degree (Degree of Substitution: DS) in accordance with the uranyl nitrate method of D. F. Durso (Methods in Carbohydrate Chem. VIII, 127–129 (1980). As a result, it was found to be 0.63, which means that 0.63 residue out of substitutable three hydroxyl groups in one glucose residue constituting a carbohydrate chain was substituted.

25 mg of the resulting partially carboxymethylated (1→3)-$\beta$-D-glucan was dissolved in 5 ml of 0.1M ammonium acetate solution and fractionated by means of GPC (column: Toyopearl HW65F, 5×100 cm, mobile phase: 0.1M ammonium acetate solution, flow rate: 5.8 ml/min). The fraction thus obtained was further subjected to GPC using different columns (columns: TSKgel G6000PW$_{XL}$+G5000PW$_{XL}$+G3000PW$_{XL}$ connected in series, mobile phase: 0.1M ammonium acetate solution, flow rate: 0.6 ml/min) to obtain sample No. 41 having a narrow molecular weight distribution (Mn=231,000).

Further, 0.3 g of the partially carboxymethylated (1→3)-β-D-glucan was dissolved in 30 ml of distilled water and the resulting solution was sonicated (9 kHz, 180–130 W, 1 hour, a sonicator, Insonator Model 201 manufactured by Kubota Works) for molecular weight reduction.

To a 4.5 ml portion of the resulting solution was added 0.5 ml of a 1M ammonium acetate solution. After mixing, fractionation by GPC and refractionation by GPC were effected in the same manner as the procedure for obtaining sample No. 41. Thus, two samples (Nos. 39 and 40) different in molecular weight were obtained.

PREPARATION EXAMPLE 10

Preparation of partially carboxymethylated (1→3)-β-D-glucan having a degree of substitution of 1.2

Ten grams of carboxymethylated (1→3)-β-D-glucan having the substitution degree (DS) of 0.63 obtained in Preparation Example 9 was added to 25 ml of a 10.5M NaOH solution at 0° C in a nitrogen gas stream to form a paste. To the resulting paste was added a monochloroacetic acid solution (10 g/12 ml) with thoroughly stirring. The mixture was heated to 60° C. and stirred for 4 hours. After cooling, 30 ml of 2M HCl was added thereto, which was then poured into 200 ml of hydrochloric acidic ethanol (40 ml HCl/ethanol). The precipitate thus formed was successively washed with 70% ethanol, ethanol and ether and dried under reduced pressure to obtain sample No. 107.

The degree of substitution was measured in the same manner as the method of measuring the partially carboxymethylated (1→3)-β-D-glucan having the DS of 0.63 obtained in Preparation Example 9. As a result, the DS of the sample was 1.20

PREPARATION EXAMPLE 11

Preparation of partially carboxymethylated laminaran

A partially carboxymethylated laminaran was prepared from laminaran derived from *Laminaria digitata* (Sigma, Lot No. 77F-3885) as in the partial carboxymethylation method in Preparation Example 9, according to the method described in A. E. Clarke and B. A. Stone: Phytochem. 1, 175 (1962) to obtain sample No. 42 (DS=0.06)

PREPARATION EXAMPLE 12

Preparation of partially methylated (1→3)-β-D-glucan

According to the method described in M. Samec, Kolloid-Beihefte 51, 369 (1940), 3.0 g of curdlan water-insoluble product obtained in Preparation Example 2 was suspended in 80 ml of water, to which 1.35 ml of saturated aqueous NaOH solution was added in a nitrogen gas stream to completely dissolve the curdlan water-insoluble product. 60 g of dimethyl sulfate was gradually added thereto at 4° C. After about one hour, the reaction mixture was added dropwise to acetone and the formed precipitate was collected. The precipitate was thoroughly washed with acetone and dried over concentrated sulfuric acid under reduced pressure to obtain 3.13 g of the above-described product (sample No. 43, DS=0.16).

PREPARATION EXAMPLE 13

Preparation of partially sulfated laminaran

*Laminaria digitata*-derived laminaran was sulfated in pyridine using a pyridine-sulfur trioxide complex (Wako Pure Chemical Industries, Lot No. PPL 8823) as described below.

0.5 g of thoroughly dried laminaran derived from *Laminaria digitata* (Sigma, Lot No. 77F-3885) was dissolved in 50 ml of dehydrated pyridine, 1 g of pyridine-sulfur trioxide complex was added thereto, and then, a reaction was effected at 60° C. for 1 hour. 100 ml of water was added to the resulting reaction mixture and the mixture was cooled followed by neutralization with NaOH. The neutralized solution was dialyzed against water using a dialysis membrane (Spectropore 1,000 cut) which had previously washed well with an aqueous alkaline solution to remove glucan. After the dialysate was concentrated, twice volume of acetone was added thereto allow a carbohydrate component to precipitate. The precipitate was washed with acetone and dried over concentrated sulfuric acid under reduced pressure to obtain 0.38 g of the above-described product (sample No. 44, DS=0.14).

A degree of substitution of methyl group(s) and sulfate group(s) in each product obtained in Preparation Examples 12 and 13 was determined and calculated according to the methods described in the following articles (1) and (2).

(1)- Ochiai, Tsuda, Sakamoto: Organic quantitative analysis (microanalysis), Nanzando (1956), (2) Whistler, R. L. ed., Methods in Carbohydrate Chemistry III, pp. 229–235, 227–280 (1964), Academic Press.

Commercially available samples

The following commercially available samples were, after determination of their physicochemical properties, subjected directly or after alkali-solubilization and neutralization to measurements.

Glucose: (WaKo Pure Chemical Industries, JIS guaranteed special grade reagent), sample No. 108

Laminarioligosaccharides: (Seikagaku Corporation, pure reagent) sample Nos. 5 to 10

Laminaran: derived from *Eisenia araborea* (Nacalai Tesque reagent), sample No. 23

Laminaran: derived from *E. araborea* (Tokyo Kasei Kogyo, reagent), sample No. 24

Laminaran: derived from *Laminaria digitata* (Sigma, reagent), sample No. 26

Lentinan: derived from *Lentinus edodes* (Aginomoto, medicine Lot No. 9Z01LS), sample No. 32

Lichenan: derived from *Cetraria islandica* (Sigma, reagent), sample No. 34

Lichenan: derived from *Usnea barbara* (Sigma, reagent), sample No. 35

Determination results of molecular weights, factor G activation inhibitory titer, etc. of the above-described samples are shown in Table-1 below.

TABLE 1

| Sample No. | Substance | Preparation Method | Carbohydrate Structure[1] | $M_n$[2] | $M_w/M_n$ | Factor G Activation Inhibitory Titer (unit/mg) |
|---|---|---|---|---|---|---|
| 1 | Curdlan GPC fraction | Preparation Example 1 | (1) | 3,050 | 1.29 | 1,000,000 |
| 2 | Curdlan water-soluble product | Preparation Example 2 | (1) | 3,270 | 2.49 | 2,240,000 |
| | Curdlan formic acid decomposition product | | | | | |
| 3 | Water-soluble fraction | Preparation Example 3 | (1) | 2,080 | 1.90 | 10,700,000 |
| 4 | Water-insoluble fraction | Preparation Example 3 | (1) | 10,000 | 3.19 | 324,000 |
| 5 | Laminaribiose | Commercially available product (Seikagaku Corporation) | (1) | 342 | | 214 |
| 6 | Laminaritriose | Commercially available product (Seikagaku Corporation) | (1) | 504 | | 4,670 |
| 7 | Laminaritetraose | Commercially available product (Seikagaku Corporation) | (1) | 667 | | 20,000 |
| 8 | Laminaripentaose | Commercially available product (Seikagaku Corporation) | (1) | 829 | | 39,800 |
| 9 | Laminarihexaose | Commercially available product (Seikagaku Corporation) | (1) | 991 | | 55,000 |
| 10 | Laminariheptaose | Commercially available product (Seikagaku Corporation) | (1) | 1,153 | | 103,000 |
| | Curdlan formic acid decomposition product | | | | | |
| 11 | GPC fraction 1 | Preparation Example 4-1 | (1) | 2,370 | 1.20 | 708,000 |
| 12 | GPC fraction 2 | Preparation Example 4-1 | (1) | 3,400 | 1.20 | 13,400,000 |
| 13 | GPC fraction 3 | Preparation Example 4-1 | (1) | 4,800 | 1.20 | 20,000,000 |
| 14 | GPC fraction 4 | Preparation Example 4-1 | (1) | 5,800 | 1.20 | 31,600,000 |
| 15 | GPC fraction 5 | Preparation Example 4-1 | (1) | 6,800 | 1.20 | 6,310,000 |
| 16 | GPC fraction 6 | Preparation Example 4-1 | (1) | 9,800 | 1.22 | 3,980,000 |
| 17 | GPC fraction 7 | Preparation Example 4-2 | (1) | 14,500 | 1.24 | 1,820,000 |
| 18 | GPC fraction 8 | Preparation Example 4-2 | (1) | 27,500 | 1.26 | 126,000 |
| | Curdlan sonicated product | | | | | |
| 19 | GPC fraction 1 | Preparation Example 5 | (1) | 20,700 | 1.27 | 646,000 |
| 20 | GPC fraction 2 | Preparation Example 5 | (1) | 28,300 | 1.18 | 389,000 |
| 21 | GPC fraction 3 | Preparation Example 5 | (1) | 50,200 | 1.26 | 4,900 |
| 22 | GPC fraction 4 | Preparation Example 5 | (1) | 58,100 | 1.29 | 234 |
| | Laminaran from | | | | | |
| 23 | Eisenia araborea | Commercially available product (Nacalai Tesque) | (2)a) | 16,800 | 1.49 | 6,760 |
| 24 | Eisenia araborea | Commercially available product (Tokyo Kasei) | (2)a) | 11,200 | 1.55 | 29,500 |
| 25 | Eisenia bycyclis | Preparation Example 6-1 | (2)a) | 22,500 | 1.27 | 64,600 |
| 26 | Laminaria digitata | Commercially available product (Sigma) | (2)b) | 5,850 | 1.16 | 7,080,000 |
| 27 | Laminaria japonica | Preparation Example 6-2 | (2)b) | 17,700 | 3.98 | 39,800 |
| 28 | Sclerotan | Preparation Example 7-1 | (2)d) | 16,800 | 2.77 | 26,300 |
| | Shizophyllan from | | | | | |
| 29 | GPC fraction 1 | Preparation Example 7-2 | (2)d) | 6,750 | 3.14 | 138,000 |
| 30 | GPC fraction 2 | Preparation Example 7-2 | (2)d) | 23,600 | 2.37 | 11,700 |
| 31 | GPC fraction 3 | Preparation Example 7-2 | (2)d) | 27,500 | 1.49 | 50,100 |
| 32 | Lentinan | Commercially available product (Aginomoto) | (2)d) | 94,700 | 1.46 | 10,000 |
| 33 | Bakers' yeast glucan water-soluble product | Preparation Example 7-3 | (2)e) | 11,600 | 5.14 | 11,500 |
| | Lichenan from | | | | | |
| 34 | Cetraria islandica | Commercially available product (Sigma) | (3) | 22,000 | 4.72 | 3,550 |
| 35 | Usnea barbata | Commercially available product (Sigma) | (3) | 23,200 | 4.07 | 120 |
| | Barley β-glucan | | | | | |
| 36 | GPC fraction 1 | Preparation Example 8 | (3) | 54,900 | 1.16 | 30,900 |
| 37 | GPC fraction 2 | Preparation Example 8 | (3) | 129,000 | 1.09 | 11,700 |
| 38 | GPC fraction 3 | Preparation Example 8 | (3) | 200,000 | 1.13 | 40,700 |
| | Partially carboxymethylated (1→3)-β-D-glucan (DS = 0.03) | | | | | |
| 39 | GPC fraction 1 | Preparation Example 9 | (1) | 42,400 | 1.14 | 117,000 |
| 40 | GPC fraction 2 | Preparation Example 9 | (1) | 77,300 | 1.10 | 91,200 |
| 41 | GPC fraction 3 | Preparation Example 9 | (1) | 231,000 | 1.10 | 80,000 |
| 42 | Partially carboxymethylated laminaran | Preparation Example 11 | (2)b) | 8,170 | 1.21 | 3,630,000 |
| 43 | Partially methylated (1→3)-β-D-glucan | Preparation Example 12 | (1) | 78,200 | 1.10 | 93,300 |
| 44 | Partially sulfated | Preparation Example 13 | (2)b) | 10,300 | 2.04 | 117,000 |

TABLE 1-continued

| Sample No. | Substance | Preparation Method | Carbohydrate Structure[1] | Mn[2] | Mw/Mn | Factor G Activation Inhibitory Titer (unit/mg) |
|---|---|---|---|---|---|---|
| 101 | laminaran Curdlan | Commercially available product (Wako Pure Chemical Industries) | (1) | 136,000< | 2.76< | 100> |
| 102 | Curdlan water-insoluble product Curdlan sonicated product | Preparation Example 2 | (1) | 159,000< | 2.50< | 100> |
| 103 | GPC fraction 5 | Preparation Example 5 | (1) | 76,300 | 1.26 | 100> |
| 104 | GPC fraction 6 | Preparation Example 5 | (1) | 92,600 | 1.23 | 100> |
| 105 | GPC fraction 7 | Preparation Example 5 | (1) | 171,000 | 1.19 | 100> |
| 106 | GPC fraction 8 | Preparation Example 5 | (1) | 216,000 | 1.19 | 100> |
| 107 | Partially carboxy-methylated (1→3)-β-D-glucan (DS = 1.20) | Preparation Example 10 | (1) | 329,000< | 1.27< | 100> |
| 108 | Glucose | Commercially available product | | 180 | | 100> |

[1] The number for the sugar chain structure is the classification number defined in the specification.
[2] Regarding glucose and laminarioligosaccharides, Mn represents an absolute molecular weight (theoretical value). Mn for others is calculated in terms of polyethylene oxide and polyethylene glycol according to the separately described molecular weight determination method.

The molecular weights in the table are represented in terms of number-average molecular weights (Mn) defined by the following formula determined by means of the above-described gel permeation chromatography (hereinafter, sometimes abbreviated as GPC). A molecular weight distribution is represented by the polydispersity (Mw/Mn) defined by the following formula;

$$\text{Number average molecular weight } (Mn) = \frac{\Sigma Hi}{\Sigma(Hi/Mi)}$$

$$\text{Weight average molecular weight } (Mw) = \frac{\Sigma(Hi \times Mi)}{\Sigma Hi}$$

$$\text{Polydispersity} = Mw/Mn$$

In the above formula, Hi represents the i-th peak height (sample concentration) when a chromatogram is equally divided by time, and Mi represents the i-th molecular weight.

The factor G activation inhibitory titer was measured according to the following activation titer determination method of factor G activation inhibiting substance and represented as units per mg. Activation titer determination method of factor G activation inhibiting substance (hereinafter, sometimes abbreviated as GI)

A 200 μl portion of a reaction mixture has the following composition.

| | |
|---|---|
| (1) Sample (note 1): GI sample or 50 μl pure water [with or without addition of 10 pg of factor G activating substance (abbreviated as GA, note 2)] | |
| (2) Limulus amoebocyte lysate proclotting enzyme fraction ($A_{280}$ = 2.5) (note 3) | 30 μl |
| (3) Limulus amoebocyte lysate factor G fraction ($A_{280}$ = 0.9) (note 3) | 20 μl |
| (4) Tris-hydrochloric acid buffer (pH 8.0) | 20 μmole |
| (5) MgCl$_2$ | 20 μmole |
| (6) Boc-Leu-Gly-Arg-pNA | 0.13 μmole |

After incubating the above-described reaction mixture at 37° C. for 30 minutes, 0.5 ml each of 0.04% sodium nitrite (0.48M HCl solution), 0.3% ammonium sulfamate and 0.07% N-1-naphthylethylenediamine dihydrochloride was added to the reaction mixture to effect coloration by diazo-coupling. The amount of released pNA was determined by measuring an absorbance at 545 nm ($A_{545}$). GI activity was calculated according to the following equation;

$$GI \text{ activity } (\%) = 100 - \frac{[A_{545} \text{ of } GI \text{ sample } (GA \text{ addition})] - [A_{545} \text{ of pure water (no } GA \text{ addition})]}{[A_{545} \text{ of pure water } (GA \text{ addition})] - [A_{545} \text{ of pure water (no } GA \text{ addition})]} \times 100$$

Under these conditions, the GI amount which causes 100% inhibition of an activation of factor G by GA is defined as 100 units.

(Note 1) Water-insoluble samples are dissolved in 0.3M NaOH and neutralized with an equal volume of 0.3M HCl.

(Note 2) GPC fractionation-purified product of the curdian sonicated product prepared in the above-described Preparation Example 5 (Table-2, No. 106, molecular weight 216,000).

(Note 3) Prepared from Japanese horseshoe crab, *T. tridentatus* according to the article [T. Obayasi et al., Clin. Chim. Acta., 149, 55–65 (1985)].

The insoluble fixation product of the present invention obtained by fixing the above-described (1→3)-β-D-glucoside structural portion on an insoluble carrier is then contacted with LAL. The contact can be carried out at 0° to 40° C., preferably 0° to 10° C., and at a pH of 6 to 8. Successively, the insoluble immobilized product is separated from LAL. The separation can be conducted by subjecting the mixture to filtration or centrifugation to remove the insoluble fixation product, or by applying LAL on a column packed with the insoluble immobilized product to obtain the passed LAL.

Since the amount of the insoluble immobilized product for contacting with LAL varies depending upon a strength of factor G activation inhibitory activity of the (1→3)-β-D-glucoside structural portion fixed on a carrier, it can be determined, for example, as follows. Under ice-cooling, various amount of the insoluble immobilized product (comprising no endotoxin) are contacted with a predetermined amount of LAL, then the insoluble immobilized product is removed by a centrifugation, to which is added a predetermined amount of a factor G activating substance (comprising no endotoxin and comprising a factor G activation inhibiting substance in an amount as small as possible) which can substantially activates LAL under ordinary determination conditions, followed by reaction under the same conditions as those usually employed when LAL is used. The amount of the insoluble immobilized product which shows 100% inhibition of an activation of LAL is determined under the above-described conditions. Then the insoluble immobilized product in the amount determined in the above is contacted with the above-described predetermined amount of LAL, successively, various amounts of the factor G activating substance are further added, whereby it is confirmed that LAL is not activated with any amount of the factor G activating substance. According to the above-described procedure, the amount of the insoluble immobilized product which is required to completely inhibit the activation of factor G in a certain amount of LAL can be determined.

The preparation of the insoluble immobilized product of the present invention as well as the preparation of LAL which specifically reacts with endotoxin utilizing the same is described by way of the following examples. The insoluble immobilized product was prepared according to the method of Matsumoto et al. (Isamu Matsumoto et al., JP-A-59-15401).

PREPARATION EXAMPLE 14

Preparation of cellulose having formic acid decomposition product (Mn, 5,800) of curdlan immobilized thereon Two grams of cellulose powder (100–200 mesh, manufactured by Toyo Roshi) was thoroughly washed with water on a glass filter, followed by suction filtration. The residue thus obtained was placed into a flask, and 30 ml of water, 13 ml of a 2M NaOH solution and 3 ml of epichlorohydrin were successively added thereto. The resulting suspension was agitated at 40° C. for 2 hours, and then thoroughly washed on a glass filter to obtain epoxy-activated cellulose. To the thus-obtained epoxy-activated cellulose (20 ml) were added 1.5 volumes (30 ml) of a 80% aqueous hydrated hydrazine solution followed by agitation at 40° C. for 1.5 hours. After the reaction, the resulting product was thoroughly washed with water on a glass filter to obtain hydrazino-cellulose. To 2 g (wet weight) of the thus-obtained hydrazinocellulose were added 1.5 ml of a 0.2M $K_2HPO_4$ solution in which 50 mg of curdlan formic acid decomposition product obtained in Preparation Example 4-1 (sample No. 14, Mn =5,800) and 26 mg of sodium cyanoborohydride were dissolved, followed by agitation at room temperature for three days. After the reaction, the resulting product was successively washed with 1 ml of water and 1 ml of an aqueous 0.2M sodium acetate solution on a glass filter. One milliliter of an aqueous 0.2M sodium acetate solution was added thereto to form a suspension and 0.5 ml of acetic anhydride was further added to the resulting suspension. After the reaction at 0° C. for 30 minutes, 0.5 ml of acetic anhydride was further added thereto and the resulting mixture was allowed to stand at room temperature for 30 minutes to thereby acetylate unreacted hydrazine residual groups. After the reaction, the resulting product was successively washed with water, a 0.1M NaOH solution, water and phosphate-buffered saline (PBS) to obtain cellulose having curdlan formic acid decomposition product immobilized thereon.

PREPARATION EXAMPLE 15

Preparation of laminaran-immobilized cellulose 20 g (wet weight) cellulose (Cellulofine, GC-700-m, available from Seikagaku Corporation) was converted to a hydrazine derivative in the same manner as in Preparation Example 14. To 2 g (wet weight) of the thus-obtained hydrazinocellulofine was added 1.5 ml of an aqueous 0.2M $K_2HPO_4$ solution in which 50 mg of laminaran derived from Laminaria digitata (available from Sigma, Lot No. 77F-3885) and 26 mg of sodium cyanoborohydride were dissolved, followed by agitation at room temperature for three days. After the reaction, the resulting product was washed, treated for acetylation of unreacted hydrazine residual groups and washed again according to the method of Preparation Example 14. Thus, laminaran-immobilized Cellulofine was obtained.

PREPARATION EXAMPLE 16

Preparation of laminaribiose-immobilized synthetic hydrophilic polyvinyl polymer One kilogram (wet weight) of Toyopearl (synthetic hydrophilic polyvinyl polymer, HW55, Fine, available from Tosoh) was treated in the same manner as in Preparation Example 14 to obtain epoxy-activated Toyopearl.

To 800 ml of the resulting epoxy-activated Toyopearl was added 1.2 l of a 0.1M $Na_2CO_3$ solution containing 92 g of adipic acid dihydrazide dissolved therein which had been adjusted to pH 9 with hydrochloric acid, followed by agitation overnight at 40° C. After the reaction, the resulting product was thoroughly washed on a glass filter with a 0.2M NaCl solution to obtain hydrazide Toyopearl. To the total amount of the resulting hydrazide Toyopearl was added 600 ml of a 0.2M $K_2HPO_4$ solution in which 32 g of laminaribiose (available from Seikagaku Corporation, Lot 8701100) and 10.4 g of sodium cyanoborohydride were dissolved, followed by agitation at room temperature for three days. After the reaction, the resulting product was successively washed with water and 0.2M sodium acetate solution on a glass filter. Thereto were added 400 ml of 0.2M sodium acetate solution and 200 ml of acetic anhydride, followed by agitation at 0° C. for 30 minutes. 200 ml of acetic anhydride was further added to the resulting suspension, which was agitated at room temperature for 30 minutes to thereby acetylate unreacted hydrazide residual groups. After the reaction, the resulting product was washed successively with water, a 0.1M NaOH solution, water and phosphate-buffered saline. Thus, laminaribiose-immobilized Toyopearl was obtained.

BRIEF DESCRIPTION OF THE DRAWINGS

The symbol ○ stands for untreated LAL and Δ stands for LAL treated in accordance with Example 2.

EXAMPLES

EXAMPLE 1

Preparation of LAL using formic acid decomposition product of curdlan immobilized on cellulose Cellulose having formic acid decomposition product of curdlan immobilized thereon (wet volume 0.4 ml) obtained in Preparation Example 14 was successively washed with 1 l of 0.1M NaOH and 1 l of distilled water to eliminate endotoxin. Distilled water was added thereto to make 2.6 ml of a suspension. 1 vial of Pregel-M main agent (Limulus test product for gelation method, freeze-dried product, Lot AB01, sensitivity 0.125 EU/ml, available from Seikagaku Corporation) was dissolved in the suspension, which was centrifuged at 3,000 rpm for 10 minutes to obtain a supernatant (LAL-1). Reactivities of the supernatant thus obtained and Pregel-M main agent dissolved in 2.6 ml of distilled water (LAL-2) to endotoxin (derived from *E. coli* 0111:B4) and to partially carboxymethylated (1→3)-β-D-glucan (Sample No. 41 obtained in Preparation Example 9, hereinafter referred to as (1→3)-β-D-glucan) was examined by checking the presence or absence of gelation according to a standard method for Pregel-M (0.1 ml of LAL was added to 0.1 ml of a sample and the mixture was allowed to stand at 37° C. for 60 minutes. The results are shown in Table-2 in which the symbols + and − mean presence and absence of gelation, respectively.

TABLE 2

| Endotoxin | 0 | 12.5 | 25 | 50 | 100 | 200 pg/ml |
|---|---|---|---|---|---|---|
| LAL-1 | −− | −− | −− | ++ | ++ | ++ |
| LAL-2 | −− | −− | −− | ++ | ++ | ++ |
| (1→3)-β-D-glucan | 0.1 | 1.0 | 10 | 100 | 1,000 | 10,000 ng/ml |
| LAL-1 | −− | −− | −− | −− | −− | −− |
| LAL-2 | −− | −− | ++ | ++ | −− | −− |

As is apparent from the Table, LAL-1 is desirably reactive with only endotoxin.

EXAMPLE 2

Preparation of LAL using laminaran-immobilized cellulose (Cellulofine)

Figure 4A:
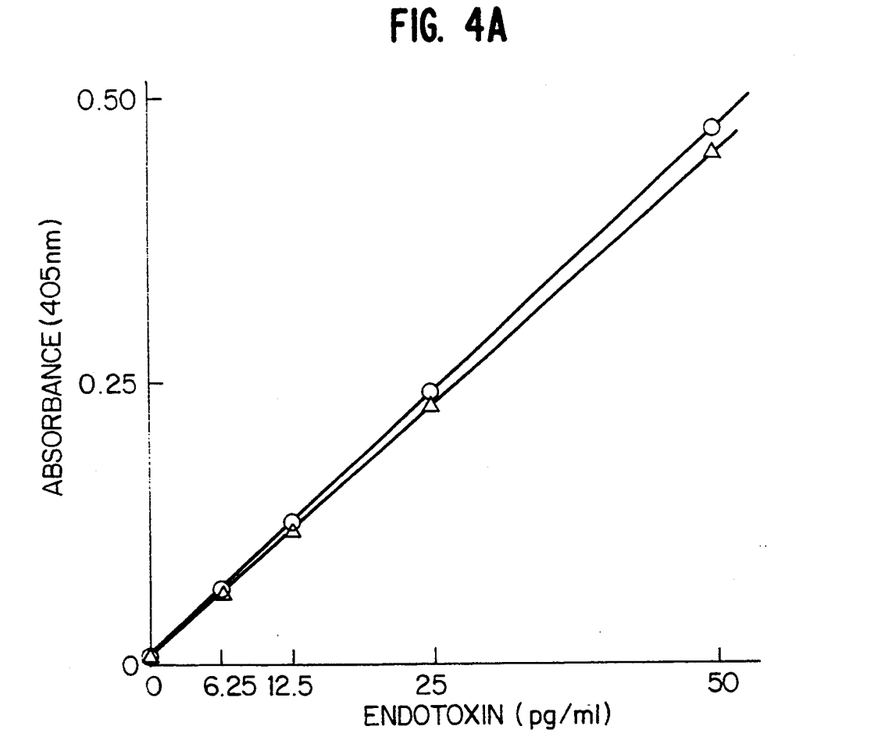
FIG. 4A shows absorbance obtained when untreated LAL or LAL treated in accordance with the present invention was reacted with various concentrations of endotoxin.
Figure 4B:
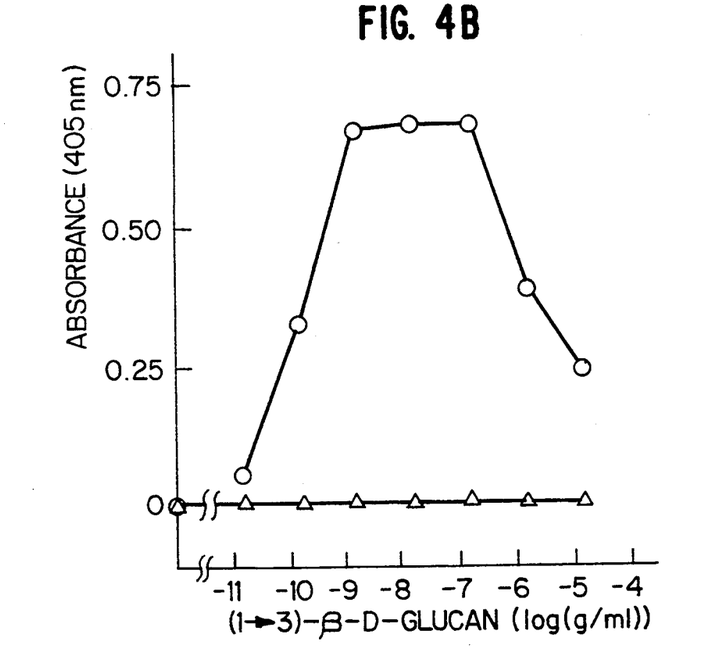
FIG. 4B shows absorbance obtained when untreated LAL or LAL treated in accordance with the present invention was reacted with various concentrations of (1→3)-β-D-glucan. The symbol ○ stands for untreated LAL and Δ stands for LAL treated in accordance with Example 2.

0.4 ml (wet volume) of laminaran-immobilized Cellulofine obtained in Preparation Example 15 was successively washed with 1 l of 0.1M NaOH and 1 l of distilled water. Distilled water was added thereto to make the total volume 4 ml. To 0.2 ml of the same was added 1.8 ml of distilled water to form a suspension, which was filtered using a polyvinylidene fluoride membrane (0.22 μm, Millex GV filter unit, available from Nihon Millipore Ltd., Lot CE11) to obtain a membrane to which laminaran-immobilized Cellulofine was adhered. Separately, limulus (*Tachypleus tridentatus*) hemolymph was collected and subjected to centrifugation (3,000 rpm, 5 minutes) to obtain hemocytes (about 20 g). 100 ml of 0.02M Tris-HCl buffer (pH 8.0) was added thereto and the mixture was homogenized with Waring blender, followed by centrifugation (8,000 rpm, 30 minutes, to separate supernatant and precipitate. This extraction procedure was repeated once again and 150 ml of the supernatant in all was obtained to serve as LAL. A 1 ml portion of the resulting LAL was filtered using the above-described membrane to which laminaran-immobilized Cellulofine was adhered to obtain a filtrate. To a 0.04 ml portion of the filtrate were added 1.5 μg of MgCl$_2$ and 4.0 μg of synthetic substrate (N-tert-butoxycarbonyl-Leu-Gly-Arg-p-nitroanilide), followed by freeze-drying. 0.1 ml of 0.2M Tris-HCl buffer (pH 8.0) and 0.1 ml of a sample (an aqueous solution of endotoxin or (1→3)-β-D-glucan in various concentrations used in Example 1) were added to the resulting freeze-dried product and the mixture was incubated at 37° C. for 30 minutes. The reaction was terminated by adding 0.4 ml of 0.6M acetic acid and an absorbance at 405 nm was measured. The results are shown in FIG. 4 as well as the results obtained using untreated LAL in the same manner. In FIG. 4, the symbol ○ stands for an absorbance obtained in the case of using untreated LAL and the symbol Δ stands for an absorbance obtained in the case of using LAL treated with laminaran-immobilized Cellulofine. As is clear from the Figure, LAL treated with laminaran-immobilized Cellulofine did not react with (1→3)-β-D-glucan but reacted with endotoxin. Thus, endotoxin can be specifically determined using the LAL treated with laminaran-immobilized Cellulofine.

EXAMPLE 3

Preparation of LAL using laminaribiose-immobilized Toyopearl 60 ml (wet volume) of laminaribiose-immobilized Toyopearl) obtained in Preparation Example 16 was successively washed with 100 ml of 0.1M NaOH and 1500 ml of distilled water on a glass filter. A 25-fold dilution of 2 ml of untreated LAL with distilled water obtained in the same manner as in Example 2 was added thereto, followed by agitation at 4° C. for 30 minutes. The mixture was subjected to a centrifugation (3000 rpm, 10 minutes). The supernatant thus obtained was freeze-dried, to which distilled water was added to make the total volume 2 ml. To a 0.1 ml portion of the same was added 0.1 ml of various concentrations of an aqueous solution of endotoxin or(1→3)-β-D-glucan and the mixture was allowed to react at 37° C. for 60 minutes. As a result, no gelation was observed when (1→3)-β-D-glucan (0.1 to 10,000 ng/ml) was added, while gelation was observed when endotoxin (100 pg/ml or more) was added.

What is claimed is:

1. A method of preparing limulus amoebocyte lysate substantially free from factor G which comprises bringing limulus amoebocyte lysate into contact with an insoluble carrier on which a (1→3)-β-D-glucoside structural portion represented by the following formula (I) produced by depolymerizing and/or fractionating a carbohydrate chain is immobilized by a method which comprises epoxy-activating an insoluble carrier with epichlorohydrin or bisoxiranes, reacting the resulting epoxy-activated insoluble carrier with hydrazine hydrate or a dihydrazide compound to obtain a hydrazine derivative or a dihydrazide derivative and bringing the

($1\rightarrow3$)-$\beta$-D-glucoside into contact with the hydrazine or dihydrazide derivative:

[I]

wherein n represents an integer of 2 to 370.

2. A method as claimed in claim 1, wherein the ($1\rightarrow3$)-$\beta$-D-glucoside structural portion additionally contains at least one structural unit selected from the group consisting of structural units represented by the following formulae (II), (III), (IV), (V) and (VI):

(II)

(III)

(IV)

(V)

(VI)

wherein at least one of $R_1$, $R_2$ and $R_3$ represents a group selected from the group consisting of a methyl group, a hydroxyalkyl group, a carboxyalkyl group, an acetyl group, a sulfate group, a phosphate group, an allyl group, a metal salt of any of said groups, an ammonium salt of any of said groups, and an organic amine salt of any of said groups, and the remaining groups represent a hydrogen atom.

3. A method as claimed in claim 1 or 2, wherein the ($1\rightarrow3$)-$\beta$-D-glucoside structural portion is derived from natural sources selected from the group consisting of ($1\rightarrow3$)-$\beta$-D-glucan derived from bacteria of the genus Alcaligenes, paramylon derived from Euglena, $\beta$-glucan or callose derived from higher plants, laminatans derived from brown algae, chrysolaminarans derived from diatoms, pachyman derived from Poria, glucan derived from the cell wall of Phytophthora, sclerotan derived from Sclerotinia, schizophyllan derived from Schizophyllum, grifolan LE derived from *Grifola frondosa*, scleroglucans derived from Sclerotium, Corticium or Stromatinia, lentinan derived from Lentinus, $\beta$-glucan derived from the cell wall of Saccharomyces (bakers' yeast), lichenans derived from Cetraria, Usnea or Evernia, and $\beta$-glucan contained in barley endosperm.

4. A method as claimed in claim 3, wherein the ($1\rightarrow3$)-$\beta$-D-glucoside structural portion is produced by depolymerizing a carbohydrate chain by a partial decomposition method selected from the group consisting of a hydrolysis using an acid, an alkali or $\beta$-glucanase, an acetolysis and a sonication, and/or fractionating a carbohydrate chain by a fractional precipitation method using an organic solvent or salts, or a fractionation method using a molecular sieve agent or a molecular sieve membrane.

5. A method as claimed in claim 1, wherein the insoluble carrier is selected from the group consisting of cellulose, agarose, crosslinked dextran, polyacrylamide, porous glass, and a hydrazine or hydrazide derivative of a synthetic hydrophilic polyvinyl polymer.

* * * * *